United States Patent [19]

Sommermeyer et al.

[11] Patent Number: 5,129,894
[45] Date of Patent: Jul. 14, 1992

[54] PACKAGE UNITS FOR MEDICAL PURPOSES

[75] Inventors: Klaus Sommermeyer, Rosbach; Jürgen Koenig, Wiesbaden; Franz Cech, Rosbach; Reinhold Herbert, Neu-Anspach, all of Fed. Rep. of Germany

[73] Assignee: Fresenius AG, Bad Homburg, Fed. Rep. of Germany

[21] Appl. No.: 229,012

[22] Filed: Aug. 5, 1988

[51] Int. Cl.$^5$ .............................................. B65D 30/08
[52] U.S. Cl. ..................................... 604/408; 604/404; 604/410
[58] Field of Search ................. 604/408, 409, 410, 403

[56] References Cited

U.S. PATENT DOCUMENTS

| | | | |
|---|---|---|---|
| 3,942,529 | 3/1976 | Waage | 604/408 |
| 4,131,200 | 12/1978 | Rinfret | 604/410 X |
| 4,636,418 | 1/1987 | Field | 604/408 |
| 4,686,125 | 8/1987 | Johnston et al. | 604/408 X |
| 4,834,721 | 5/1989 | Onohara | 604/266 |
| 4,837,047 | 6/1989 | Sato et al. | 604/410 X |

*Primary Examiner*—Robert A. Hafer
*Assistant Examiner*—Kerry Owens
*Attorney, Agent, or Firm*—Pravel, Gambrell, Hewitt, Kimball & Krieger

[57] ABSTRACT

The present invention describes package units for medical purposes, in particular for receiving and/or storing sterilizable preparations for parenteral uses or dialysis solutions, comprising a container having at least one discharge spout and consisting of polyamide 66 or a laminate of polyamide 66 sheet and polyolefin sheet, the polyolefin sheet being disposed on the side facing the liquid to be stored and the sheet of polyamide 66 being disposed on the outside and the two sheets being bonded together in usual manner by means of an adhesive. The package units may further comprise an inner container or an outer container. The package unit is made in that a container having at least one discharge spout is made from polyamide 66 or the aforementioned laminate, said container filled with the liquid to be stored, then sealed and sterilized and possibly subsequently surrounded after cooling and drying with an outer container of polymeric material. Package units according to the invention may also be made in that from a polymeric material an inner container having at least one discharge spout is made, said container filled with the liquid to be stored, sealed, then surrounded with an outer container of polyamide 66 or a laminate of polyamide 66 sheet and polyolefin sheet, the polyolefin sheet being disposed at the side of the laminate facing the inner container and the sheet of polyamide 66 of the laminate representing the outer sheet, and thereafter sterilized.

20 Claims, 1 Drawing Sheet

PACKAGE UNITS FOR MEDICAL PURPOSES

The subject of the present invention is package units for medical purposes, in particular for receiving and/or storing sterilizable preparations for parenteral use of dialysis solutions, including a container having at least one discharge spout and consisting of a polymeric material including polyamide, which possibly have also an inner container or an outer container, and method for the production thereof.

It has been known for a long time to employ package units, for example bags, in particular for medical purposes for storing preparations for parenteral use or dialysis solutions, instead of glass bottles, for receiving and sterile storing of infusion solutions to be administered parenterally or of dialysis solutions. For this purpose these bags must be completely sterile and this is usually achieved by heating to at least 100° C., in particular to about 120° C.

This leads directly to the requirement made of the thermoplastic polymeric material that the latter be stable at least up to the heating temperature. In addition, such a storage bag must be easy to make in economical manner in an automatic production process and disposable after use because of its low value. It should also be flexible, foldable and in the processed state transparent so that changes of the liquid contained in the bag can be immediately noticed.

As material for filling these requirements preferably soft PVC containing plasticizer to improve its elastic properties was employed. These plasticizers, for example diisoctylphthalate, are however the cause of worrying phenomena, said plasticizers of softeners are not completely enclosed in the voids between the polymeric chains and can therefore be dissolved out of the polymer by the water or aqueous solution introduced into the bag so that contamination of the liquid contained in the bag occurs. Estimates have shown that a patent treated for a relatively long time using such PVC bags will have absorbed a few g plasticizer and this in itself is extremely worrying physiologically and can lead to permanent damage in the patient. Moreover, such a bag consisting of soft PVC easily be attacked by microorganisms which in particular dissolve out the plasticizers and thus regularly destroy the bag. To prevent this, after filling such a PVC bag had to be protected from harmful organisms by a special surrounding package.

These facts led to such PVC bags not being able to supersede to an appreciable extent the glass bottles used normally as storage containers for medical solutions and even not being allowed at all in the field of medicine in some industrial countries.

Attempts have therefore been made to replace the soft PVC by other materials. However, such attempts failed because these materials were either too expensive or had mechanical and physiological disadvantages. For example, their water permeability was too high and this led to an undesirable increase of the concentration of the substances contained in the solution. In addition, lixiviatable substances were liberated from them or they were easily damaged under excessive mechanical stress. CH-PS 444,382 describes such a plastic bag which can be used for therapeutical solutions to be employed parenterally. In this plastic bag the wall consists of a plastic laminate which comprises on the outside, i.e. the side remote from the liquid, a PVC layer and on the inside a polyhalogen hydrogen synthetic resin layer. The latter layer does not have any pharmacologically inadmissible constituents which by dissolving might pass into the solution contained in the bag. However, the polyhalogen hydrocarbon substances employed have the disadvantage that they are very expensive to produce and process and do not fuse adequately at the welds so that there is still a direct contact with the PVC. This contact also exists moreover at the discharge opening which is usually completely made of PVC and with which further PVC compound flexible tubes can be connected. Moreover, as disposable bag these plastic bags represent an environmental hazard because burning of said bags leads to highly aggressive hydrocarbons.

Polyolefins, e.g. polyethylene, have also already been proposed as materials for the storage package. Polyolefins are free from plasticizer and are thus not attacked by microorganisms. In addition, they have a good water vapour barrier and are sterilizable. Bags of polyolefins are described for example in DE-PS 3,200,264 and DE-PS 3,305,365.

These bags of polyolefins unfortunately however have the disadvantage that they have a relatively high oxygen permeability and this is problematical in the storage of solutions which must be kept for relatively long times in so far as due to the oxygen permeability oxidation of the dissolved constituents can occur. This is in particular extremely critical with amino acid solutions and must therefore be avoided. To overcome this problem it has been proposed according to DE-PS 3,200,264 and DE-PS 3,305,365 to coat the bag sheet of polyolefin on its outside with one or more layer(s) reducing this oxygen permeability, for example of a metal foil or a further polymer. Such a coating is also used for safety reasons because even on extremely careful production the bag sheet can have pinholes which cannot be seen and which can impair the sterility of the solution introduced. In addition, such a covering or coating can also considerably improve the mechanical loadability of such a bag so that such a bag even when dropped from a height of several metres does not burst. The sheet or layer used is one having a higher melting point than the polymer facing the solution, i.e. which at the melting temperature of the inner sheet does not itself melt and consequently will not stick to a sealing tool either. Such an outer sheet can thus also serve as parting agent in the sealing of the inner sheet. Named as preferred polymers for coating the polyolefin sheet are polymers having a low water vapour permeability and a low oxygen permeability, such as polyamides, and as polyamide polycaprolactam (PA 6) is preferred, containing no stabilizing additives and thus complying in its composition with the requirements for use in the foodstuff sector.

As however recent investigations on bags of such polyolefin/polyamide laminates have shown the laminates of polyolefin and polyamide, such as laminates of polyethylene and polycaprolactam, have disadvantages in that undesirable toxic foreign constituents are released into the liquids to be stored in the sterilization and render the solution unemployable for its intended use, for example the injection. As it has been possible to show, these foreign constituents reach the liquid to be stored by migration from the outer sheet of the laminate through the inner sheet of the laminate facing the liquid.

Bags of such laminates are therefore extremely dubious from the medical point of view.

Accordingly, the problem underlying the present invention is to provide package units of the aforementioned type which do not have the disadvantages of the known package units or bags, are unobjectionable from the medical point of view and in which no migration of foreign constituents into the solution to be stored takes place, and which furthermore are mechanically stable, transparent and heat-sterilizable and have low water vapour permeability and low oxygen permeability and in addition cannot be attacked by microorganisms.

According to the invention this problem is solved in that as polyamide polyamide 66 is employed.

Under the term "polymeric material including polyamide" herein polyamide or polyamide-containing laminate of polymeric material is meant. Thus, according to the invention the container of the package unit according to the invention may consist both only of polyamide 66 and of a laminate of polymeric material including polyamide 66.

Polyamide 66 (PA 66) means the polycondensate obtained by polycondensation of hexamethylene diamine and adipic acid.

It has surprisingly been found according to the invention that when using polyamide 66, in contrast to the other polyamides, for example polyamide 6, polyamide 11, polyamide 12 or polyamide 13, as polymeric material for the container for the package unit after the sterilization no foreign constituents or no ponderable amounts of foreign constituents are to be found in the liquid to be stored. The same is true when as polymeric material for the containers of the package unit polyamide 66 is employed in the laminate with polyolefin sheets, the polyolefin sheet being disposed on the side facing the liquid to be stored and on the outside the sheet of polyamide 66, the two sheets being bonded together in usual manner by means of an adhesive. Whereas for example in using bags of a laminate of polyethylene and polyamide 6, the polyethylene sheet being used as inner sheet and the polyamide 6 sheet as outer sheet, after sterilization in the liquid to be stored foreign constituents were found in an amount of 5 to 15 ppm, the respect to the product, under the same conditions for bags made from a laminate of polyethylene and polyamide 66, the polyethylene sheet being disposed on the side facing the liquid and the polyamide 66 sheet on the outside, no or no ponderable amounts (weighing accuracy <1 mg) of foreign constituents could be found in the liquid to be stored.

According to a preferred embodiment as material for the container of the package unit according to the invention the polyamide 66 is used in a laminate with a polyolefin, the polyolefin sheet being disposed on the side facing the liquid to be stored and the polyamide 66 sheet on the outside and the two sheets being bonded together in usual manner by means of an adhesive.

As polyolefins which for making the package unit according to the invention can be used as polymer for the inner sheet, according to the invention polymers of olefins are suitable, such as ethylene, propylene, butylene and the like, which are possibly substituted. As substituents for example the methyl or ethyl group, the vinyl group and halogen atoms, in particular fluorene or chlorine atoms, may be present. Preferably employed as starting olefin are ethylene and propylene, in particular ethylene polymerized to polyethylene being employed.

Specific examples for polyolefins are: polyethylene, polypropylene, poly-n-butylene, polyisobutylene, poly-4-methylpentene-1, chlorosulfonated polyethylene, polystyrene, halogenated polyethylene, such as polyvinyl fluoride, polyvinylidene fluoride and polyvinylidene chloride, polymethylmethacrylate and the like. The olefins employed for making the above polyolefins may also be used as copolymers and mixed polymers with other vinyl compounds, for example ethylene/propylene plastics, poly (ethylene/vinyl acetate), acrylonitrile/butadiene/styrene polymers, ethylene-propylene block copolymers, styrene copolymers, copolymers containing vinylidene fluoride and copolymers containing styrene.

According to the invention polyolefins are products which are made by the vinyl polymerization of possibly substituted olefin, preferably ethylene. These products may also have slight additives of other polymers which do not essentially destroy or change the structure of said polyolefins. Thus, for example, small amounts of styrene-substituted or polyacrylonitrile-substituted ethylene compounds may be added. The resulting polyolefin products are considered as belonging to the polyolefins specified above.

According to the invention, as polyolefin preferably polyethylene is used as material for the inner sheet, possibly with slight additions of vinyl acetate in the form of the copolymer of ethylene and vinyl acetate.

In such a case for example the vinyl acetate content may be up to 10% by weight.

In particular a polyethylene is used of medium or high density (MDPE and HDPE) which is usually made by low-pressure polymerization. The density lies within a range of 0.91 to 0.94 g/cm$^3$, in particular about 0.935 g/cm$^3$.

Furthermore, the polyethylene preferably used according to the invention has a high molecular weight and a narrow molecular weight distribution.

It is however to be ensured in every case that such polyolefins do not have a melting point below the sterilization temperature of about 110°-120° C. Preferably, the melting range should be above 110° C.

For making the sheets suitable for the laminates the usual extruding method of making sheets or hose sheets can be employed and do not present the expert with any appreciable problems. The polymeric inner sheet and the polymeric outer sheet are bonded together in a manner known per se. Any known method suitable for making the laminates according to the invention can be employed. Preferably, the inner and outer sheets are adhered together by means of a laminating adhesive such as polyvinylidene chloride or a polyurethane. Such a polyurethane adhesive can advantageously be a two-component adhesive, the first component consisting of a laminated adhesive and the second component of an additive lacquer.

In the production technique the polyolefin used as inner sheet can be extruded in the form of a hose-like sheet and thereafter adhered to the laminated sheet of polyamide 66 using the laminating adhesive mentioned above, polyurethane being preferred.

Figure 1:
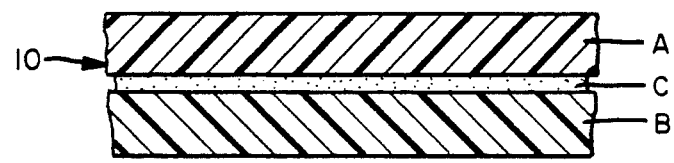
FIG. 1 is a side view in cross-section of a polymeric laminate material according to the present invention.

Preferred laminates have at a temperature of about 23° C. and a relative air humidity of 85% as a rule a water vapour permeability according to DIN 53122 of <1. Such values apply to standard laminates which are advantageously up to 0.2 mm thick, with a thickness of 50 to 150 μm, in particular about 100 μm, for the polyolefin sheet and 20 to 100 μm, in particular 30 to 80 μm, for the polymeric laminating sheet of polyamide 66. For example, a particularly suitable laminate consists of a 130 μm thick polyethylene sheet and a 50 μm thick sheet of polyamide 66.

In the laminates according to the invention, particularly in the preferred laminates, the oxygen permeability is reduced, this value lying below 15 cm$^3$/m$^2 \times$ day $\times$ bar pressure difference.

The sheets used according to the invention for making the laminate have been approved both by the Federal Health Office in Berlin and by the FDA (Federal Drug Administration) in the U.S.A. as physiologically harmless for use in the foodstuff sector and in the medical sector.

The laminates of polyolefin and polyamide 66 used for the package units according to the invention are free from plasticizers and additives or constituents which might possibly be physiologically objectionable and in particular could diffuse or migrate into the aqueous solution. The laminates used according to the invention are heat-sterilizable, clear and transparent and also have these properties after the sterilization.

Furthermore, they are mechanically stable and have low vapour permeability and a high oxygen barrier effect.

The package units according to the invention or the containers of said package units according to the invention may have any suitable shape or form. Expediently, they are made in the form of bags.

The package units or containers or bags according to the invention have at least one discharge spout or outlet nozzle which is formed in hose manner or includes a tube piece or insert piece. The latter may consist of respectively suitable material and can be formed in any desired manner and secured in the container or bag. For example, they may be formed in the manner described in DE-PS 3,305,365 and DE-PS 3,200,264, to which reference is made hereby, and consist of the materials specified therein.

The production and processing of the materials for the package units or containers according to the invention is carried out by the methods usual in plastics technology, as already explained above. Thus, for example, the containers may be made by an extrusion of hose-like sheets, corresponding cutting to size of the sheets and lamination and subsequent edge welding thereof. The containers, in which the edge provided for the discharge spout remains unwelded, are subsequently fused to a tube piece possibly comprising a bonding layer or an insert piece comprising the discharge opening(s) and possibly surrounded by a bonding layer. When using a bonding layer as described for example in DE-PS 3,305,365 the tube or insert piece is provided with such a bonding layer in accordance with the usual techniques, as can be done for example by simply drawing on or pushing over the elastic material of the bonding layer in hose form onto the tube piece or insert piece and introducing it into the opened container. Thereafter the heat sealing of the entire still not welded edge to the hose connection piece or to the tube piece or insert piece provided with the bonding layer is carried out. If several tube pieces are provided this processing step is carried out simultaneously, corresponding sealing tools being of course employed. The heat sealing is carried out by the usual methods.

The sterilization of the containers thus made is by the usual methods in an autoclave and of course to avoid bursting of the containers in the autoclave an excess pressure must be applied to balance the pressure obtaining in the container interior. For safety reasons and, if a bonding layer is employed, to fix the bonding layer, however, a higher excess pressure is used than would be necessary to balance the pressure obtaining in the container interior. The excess of this pressure over the pressure obtaining in the container is not critical but for example it should be at least 0.5 bar greater than the pressure obtaining in the container. It may be 2 to 3 bar, for example 2.2 bar.

If this is necessary due to the materials employed, the laminates according to the invention can further be subjected to a crosslinking after the sealing of the containers, before the liquid to be stored is introduced and before the sterilization.

In the cases where a crosslinking of the welded container material comprising discharge spouts with hose connection pieces or tube or insert pieces is intended, said crosslinking is carried out before the sterilization, if a sterilization is then still necessary, by methods known per se as described for example in DE-PS 3,200,264 and EP-PS 0 068 271.

In accordance with a further embodiment, in particular in cases where a particularly high protection against mechanical damage is to be obtained and/or for long-time storing of the package units, the container of the package unit according to the invention may be surrounded by a further container, an outer container.

Suitable materials for such a further container or outer container are materials which are able to protect the container according to the invention, which when using an outer container represents the inner container, from mechanical damage, avoid any water vapour losses, prevent access of microorganisms (no fungus formation or sporulation), represent a gas barrier, i.e. oxygen barrier, are preferably substantially transparent and permit a long-time storage of the package units.

Examples of such materials are metal or plastic foils or laminates which fulfil the aforementioned conditions. Preferred are foils or laminates of plastic.

Examples for metal foils or laminates are:
aluminium foils,
laminates of polyethylene sheets and aluminium foils,
laminates of polypropylene sheets and aluminium foils.

Suitable as plastics are essentially the polyolefins as names above in conjunction with the containers according to the invention, which when using outer containers represent the inner containers. Said plastics may be used in the form of individual sheets or in the form of laminates of two or more sheets. Preferred are laminates of two sheets: inner sheet, i.e. the sheet facing the inner container, and outer sheet, i.e. the outer foil or sheet coming into contact with the environment.

Particularly suitable according to the invention for the outer container are laminates of polyolefins as named above for the inner container, polyethylene being particularly preferred as polyolefin, and polyesters, copolymers of ethylene and vinyl alcohol, copolymers of ethylene and vinyl acetate. Examples of suitable laminates are laminates of polyethylene sheet and polyester sheet, as polyester polyethylene terephthalate and polybutylene terephthalate being particularly suitable, laminates of polyethylene sheet and a sheet of copolymers of ethylene and vinyl alcohol, laminates of polyethylene sheet and a sheet of copolymers of ethylene and vinyl acetate.

According to the invention this outer container further provides a double oxygen barrier and the container contents, i.e. the liquid or solution to be stored, are protected from oxidation.

In the production of these package units according to the invention comprising outer container firstly the inner container is made as described above; when using a laminate of a polyamide 66 sheet and a polyolefin sheet the polyolefin sheet is arranged on the side facing the liquid to be stored and the sheet of polyamide 66 is arranged on the outer side and the two sheets are bonded together by means of an adhesive. Thereafter the inner container thus made, possibly after crosslinking, is filled with the liquid or solution to be stored, sealed and sterilized as described above. After cooling and drying of said sterilized inner container the sealed and sterilized inner container filled with the liquid to be stored is provided in a manner known per se with the outer container.

For example, the sterlized dried and cooled inner container is placed in a lower web deep-drawn corresponding exactly to its contours for the outer container and covered with the upper web for the outer container. Thereafter, a vacuum is applied to the outer container, which should be about 900 to 900 mbar. At the same time or directly thereafter the edges of the upper web and lower web of the outer container are welded together. When the vacuum is applied the sheet of the outer container bears sealingly on the laminate of the inner container.

The lower web and the upper web may consist of the same or different material and consist preferably of the same material. Likewise, the upper web and the lower web of the outer container may have the same or different thicknesses and are preferably of the same thickness. It is important for the materials of the lower web and upper web to be weldable together, in the case of laminates the inner layers of the lower web and upper web. If the lower web is deep-drawn said lower web should be preferably somewhat thicker than the upper web. The upper web and the lower web have expediently thicknesses of 100 to 200 $\mu$m.

In accordance with a further embodiment of the package units of the invention the container referred to above and consisting of polyamide 66 or a polymeric laminate including polyamide 66 may represent the outer container and surround an inner container of polymeric material having at least one discharge spout; when using a laminate including polyamide 66 for the outer container the side of the laminate facing the inner container consists of polyolefin sheet and the outer side of the laminate of polyamide 66 sheet and the two sheets are bonded together in the usual manner by means of an adhesive.

As material for the inner container according to this embodiment any polymeric material may be used which is suitable for storing and keeping the sterilizable preparations for parenteral use or the dialysis solutions, permits sterilization and has no migratable substances. The container material may be in the form of individual sheets or in the form of laminates and is preferably substantially transparent. Examples of such materials are: polyolefins, polyesters and copolymers thereof. The polyolefins include the polyolefins mentioned above, including PVC and soft PVC, polyethylene being preferred. As polyester polyethylene terephthalate is for example suitable.

Particularly preferred as material for the inner containers according to this embodiment, in the form of individual sheets or laminates, are polyethylene, copolymers of ethylene and propylene and polyester, such as polyethylene terephthalate.

Suitable laminates are composite sheets of the aforementioned materials, possibly with embedded ethylene/vinyl alcohol (EVAL) barrier layers. Examples of suitable laminates are laminates of polyolefin sheets, in particular polyethylene, laminates of polyethylene sheet and polyester sheet, polyethylene terephthalate being particularly suitable as polyester, laminates of polyethylene sheet and sheet of copolymers of ethylene and vinyl alcohol, laminates of polyethylene sheet and sheet of copolymers of ethylene and vinyl acetate.

The production of the package units according to this embodiment is carried out in that firstly the inner container with at least one discharge spout, as described above, is made from the materials specified above and then, possibly after any necessary crosslinking, filled with the liquid or solution to be stored and subsequently sealed. Thereafter the inner container filled with liquid and sealed is provided with the outer container of polyamide 66 or a polymeric laminate including polyamide 66, when using a laminate including polyamide 66 for the outer container the side of the laminate facing the inner container consists of polyolefin sheet and the outer side of the laminate consists of polyamide 66 sheet, and the two sheets are bonded together in the usual manner by means of an adhesive and thereafter subjected to the sterilization as described above.

For example, the method is carried out in such a manner that the sealed inner container filled with the liquid or solution to be stored is placed in a deep-drawn lower web for the outer container corresponding exactly to its contours and covered with the upper web for the outer container and thereafter a vacuum which should be about 900 to 980 mbar is applied to the outer container. Simultaneously or directly thereafter the edges of the upper web and lower web of the outer container are welded together. When the vacuum is applied the sheet or laminate of the outer container comes to lie sealingly on the inner container. The lower web and the upper web of the outer container may consist of the same or different material and consist preferably of the same material. Likewise, the upper web and the lower web of the outer container may have the same or different thickness and are preferably of equal thickness. The important point is that the materials of the lower web and upper web, in the case of laminates the inner layers of the lower web and upper web, are weldable together. If only the web is deep-drawn said lower web should preferably be somewhat thicker than the upper web. The upper and lower web expediently have thicknesses of 100–200 $\mu$m.

The package unit thus made filled with the liquid or solution to be stored and sealed and comprising the inner and outer containers is thereafter sterilized in a pressure autoclave at a temperature of about 120° C. and an excess pressure of about 2.2 bar.

It has surprisingly been found that when using the outer containers as described above, in particular consisting of a laminate of a polyethylene sheet and a sheet of polyamide 66, the polyethylene sheet being disposed on the side of the laminate facing the inner container and the sheet of polyamido 66 on the outside of the laminate and the two sheets being bonded together in usual manner by means of an adhesive, after the procedure according to the invention package units or containers are obtained in which no or substantially no migration into the liquid to be stored and no oxidation of the liquid to be stored occurred. Likewise, no microorganisms were found.

Referring now to FIG. 1, a polymeric laminate material 10 according to the present invention has a sheet A of polyamide 66 which is bonded to a sheet B of polyolefin by an adhesive layer C.

Figure 2:
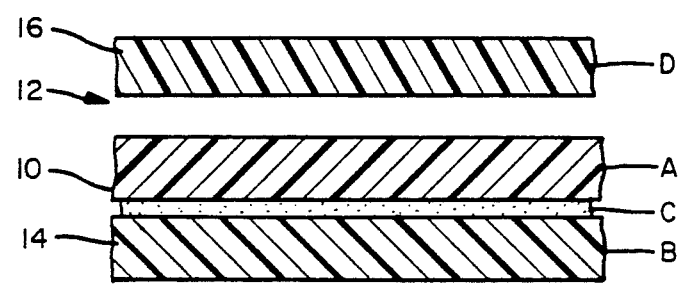
FIG. 2 is a partial side view in cross-section of a package unit according to the present invention.

FIG. 2 partially illustrates a package unit 12 according to the present invention which has a first inner container 14 made from a polymeric laminate 10 (as in FIG. 1) disposed in a second container 16 made from a sheet D, preferably a metal or plastic foil or a polymeric laminate. In a preferred embodiment, as previously described, the sheet D bears sealingly against, but is not bonded to, the sheet A.

Figure 3:
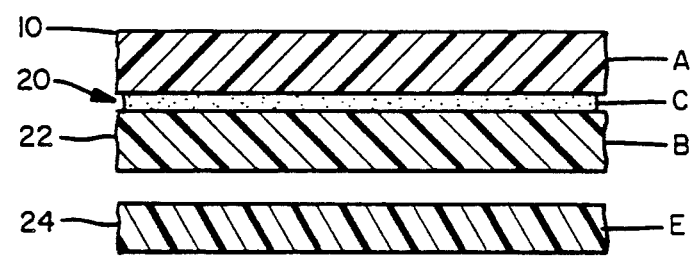
FIG. 3 is a partial side view in cross-section of a package unit according to the present invention.

FIG. 3 partially illustrates a package unit 20 according to the present invention which has a first container 20 22 made from a polymeric laminate 10 in which is disposed a second container 24 made from a sheet E, preferably a polymeric material. In a preferred embodiment, the sheet B lies on, but is not bonded to, the sheet E.

The following examples serve for further explanation of the invention.

EXAMPLE 1

From a laminate of polyethylene and polyamide 66, made by bonding together a commerically available polyethylene sheet (density 0.93 g/cm$^3$) and a commercially available sheet of polyamide 66 (density 1.13 g/cm$^3$, melting point 255° C.) by means of polyurethane as laminating adhesive, storage bags for infusion solution were made having a capacity of a bout 1 l, the laminate having been edge welded except for the discharge openings and a tube piece of polycarbonate having a bonding layer of a copolymer of ethylene and vinyl acetate with a vinyl acetate content of 28% inserted into the discharge opening and secured by means of heat sealing. In these bags the polyethylene sheet represents the inner sheet and the sheet of polyamide 66 the outer sheet. The bag thus made was filled with infusion solution, sealed and introduced into a pressure autoclave where it was sterilized at a temperature of about 120° C. and an excess pressure of about 2.2 bar. The laminate had a thickness of 180 μm, the polyethylene sheet being 130 μm thick and the polyamide 66 sheet 50 μm thick.

The storage bag thus made is transparent.

In investigations using the bag made in this manner it was found that in the infusion solution contained in said bag even after the sterilization carried out as described above no foreign constituents could be found in ponderable amounts (weighing accuracy <1 mg).

These investigations were carried out in the following manner:

A bag of 1 l capacity was filled with water ad injection (1 part distillate, highly pure) and sterilized for 121° C. (holding time: 10 min) with an $F_0=16$. After cooling the bag content was evaporated to dryness at 40° C. in a rotary evaporator and any residue obtained weighed.

Compared with the bag made according to the invention above as set forth in Example 1, with a bag made in the same manner and consisting of the same material, with the exception that instead of polyamide 66 polyamide 6 was used, in the same investigations a residue of foreign constituents of 5 to 15 ppm was found.

These values show that with the bag according to the invention compared with bags having polyamide 6 instead of polyamide 66 no migration of foreign constituents into the infusion solution took place.

EXAMPLE 2

Corresponding to the method described in Example 1 an inner bag having a capacity of about 1 l was made from polyethylene sheet (thickness 130 μm), the sheet edge welded except for the discharge openings and a tube piece of polycarbonate comprising a bonding layer of a copolymer of ethylene and vinyl acetate with a vinyl acetate content of 28% was introduced into the discharge opening and secured by means of heat sealing. The bag (inner bag) made in this manner was filled with infusion solution, sealed and, without previous sterilization, placed on a deep-drawn lower web of an outer bag or surrounding bag with contours exactly corresponding to those of the inner bag and covered with the upper web. Thereafter a vacuum of 950 mbar was applied to the outer or surrounding bag as subsequently the lower web and the upper web of the outer or surrounding bag were welded together along the edges.

The upper web and the lower web of the outer or surrounding bag each consisted of a laminate of polyethylene sheet and a sheet of polyamide 66 as was used for making the bag according to Example 1. The sheet of the laminate of the outer bag facing the inner bag consisted of polyethylene and the outer sheet of the laminate of the outer bag consisted of polyamide 66. The laminate for the lower web had a thickness of 1.25 μm, the ethylene sheet having a thickness of 75 μm and the sheet of polyamide 66 a thickness of 50 μm. The thickness of the laminate of the upper web was 1.25 μm, the polyethylene sheet having a thickness of 75 μm and the sheet of polyamide 66 a thickness of 50 μm.

The package unit made in this manner, filled with infusion solution and sealed and comprising an inner and outer bag was subsequently introduced into a pressure autoclave and there sterilized at a temperature of about 120° C. and an excess pressure of about 2.2 bar.

The package unit obtained and comprising the outer or surrounding bag of a laminate of polyethylene sheet and a sheet of polyamide 66 was transparent and even after sterilization and long storage permitted excellent visual inspection for the infusion solution contained in the bag. As was determined by the investigation carried out as described above in Example 1, in the infusion solution surrounded by the inner bag and the outer bag even after sterilization no foreign constituents were detected in ponderable amounts (weighing accuracy <1 mg). The stored infusion solution remained clear. No migration of foreign constituents occurred and no oxidation products or any other microorganisms (fungus formation or sporulation) of any kind were found.

Investigations as have been described above have shown that compared therewith in a package unit made up in the same manner and of the same material but employing polyamide 6 instead of polyamide 66 for the laminate for the outer or surrounding bag a residue of foreign constituents of about 5 to 15 ppm occurred in the infusion solution after the sterilization.

We claim:

1. A package unit for medical purposes, in particular for receiving or storing a sterilizable liquid preparation for parenteral use or dialysis solutions, the package unit comprising a first container consisting of a polymer laminate material which comprises on the side facing the liquid preparation a polyolefin sheet and on the other side a sheet of polyamide 66, the two sheets bonded together by means of an adhesive, a second container outside of and surrounding the first container, the second container bearing sealingly on, without bonding to, the polymeric laminate material of the first container, and the package unit having at least one discharge spout for discharging the liquid preparation therefrom.

2. The package unit according to claim 1, wherein the polyolefin sheet is a polyethylene or polypropylene sheet.

3. The package unit according to claim 1, wherein the polyolefin sheet and the sheet of polyamide 66 are bonded together by means of a polyurethane adhesive.

4. The package unit according to claim 1, wherein the polymeric laminate material is up to 0.2 mm thick, the polyolefin sheet having a thickness of 50 to 100 μm and the sheet of polyamide 66 a thickness of 20 to 100 μm.

5. The package unit according to claim 1, wherein the outer container consists of a polymeric material.

6. The package unit according to claim 5, wherein the outer container consists of a polymeric laminate.

7. The package unit according to claim 1, comprising also a third container in which the liquid preparation resides and having an exterior surface and having an interior with which the at least one discharge spout communicates the third container enclosed and surrounded by the first container.

8. The package unit according to claim 7, wherein the polyolefin sheet faces, without bonding to, the exterior surface of the third container.

9. A package unit according to claim 8, wherein the third container consists of polyolefin, polyesters or copolymers thereof.

10. A package unit for receiving or storing a sterilizable liquid preparation for parenteral use or dialysis solutions, the package unit comprising a first container consisting of a polymeric laminate material which comprises on the side facing the liquid preparation a polyolefin sheet and on the other side a sheet of polyamide 66, the two sheets bonded together by means of an adhesive.

a second container inside of and surrounded by the first container, the polymeric laminate material of the first container, facing, without bonding to, the second container, and the package unit having at least one discharge spout for discharging the liquid preparation therefrom.

11. A method for making a package unit for receiving or storing a sterilizable liquid preparation for parenteral use or dialysis solutions, the method comprising making a first container consisting of a polymeric laminate material which comprises on the side facing the liquid preparation a polyolefin sheet and on the other side a sheet of polyamide 66, by bonding the two sheets together by means of an adhesive, filling said first container with the liquid preparation, then sealing and sterilizing said first container, disposing said first container in a second container and sealing the first container in the second container so that the second container bears sealingly on, without bonding to, the first container.

12. The method according to claim 11, wherein the polyolefin sheet is polyethylene foil.

13. The method according to claim 11, wherein said first container is sterilized at a temperature of about 120° C. and an excess pressure of about 2.2 bar.

14. The method according to claim 11, wherein said first container after sterilizing is allowed to cool and dry and is thereafter disposed in said second container.

15. The method according to claim 14, wherein said second container is made from a polymeric material.

16. A method for making a package unit for receiving and storing a sterilizable liquid preparation for parenteral use or dialysis solutions, the method comprising making an inner container and an outer container, making the outer container from a polymeric material including polyamide 66, the polymeric material including a laminate of polyolefin sheet and an outer sheet of polyamide 66, the polyolefin sheet being arranged at the side of the laminate facing the liquid preparation, making the inner container from a polymeric material, filling the inner container with the liquid preparation, sealing and thereafter surrounding the inner container with the outer container, the outer container bearing sealingly on, without bonding to, the inner container, and emplacing at least one discharge spout in the package unit for discharging the liquid preparation therefrom.

17. The method according to claim 16 wherein the polyolefin sheet is a polyethylene sheet.

18. The method according to claim 16 wherein the inner container is made from polyolefin, polyester or copolymers thereof.

19. The method according to claim 16, wherein the polymeric material for the outer container is a laminate of a polyolefin sheet and a sheet of polyamide 66 which are bonded together with an adhesive, the polyolefin sheet arranged at the side of the laminate facing the inner container and the sheet of polyamide 66 of the laminate being the outer sheet.

20. A method for making a package unit for medical purposes for receiving or storing sterilizable liquid preparations for parenteral use or dialysis solutions, the method comprising making a first container from a polymeric laminate material which comprises on the side facing the liquid preparation a polyolefin sheet and on the other side a sheet of polyamide 66, by bonding the two sheets together by means of an adhesive, disposing a second container within said first container, filling said second container with the liquid preparation, then sealing and sterilizing said second container, sealing the second container in the first container so that the first container lies on, without bonding to, the second container, and emplacing at least one discharge spout in the package unit for discharging the liquid preparation therefrom.

* * * * *